(12) United States Patent
Peppel

(10) Patent No.: US 8,100,866 B2
(45) Date of Patent: Jan. 24, 2012

(54) NEEDLELESS ACCESS PORT VALVES

(75) Inventor: Peter W. Peppel, Nazareth, PA (US)

(73) Assignee: B. Braun Medical Inc., Bethlehem, PA (US)

(*) Notice: Subject to any disclaimer, the term of this patent is extended or adjusted under 35 U.S.C. 154(b) by 1891 days.

(21) Appl. No.: 11/089,183

(22) Filed: Mar. 24, 2005

(65) Prior Publication Data
US 2006/0217671 A1 Sep. 28, 2006

(51) Int. Cl.
A61M 5/00 (2006.01)

(52) U.S. Cl. .......... 604/246; 604/288.03; 604/6.1; 604/99.04; 604/256

(58) Field of Classification Search .......... 604/284, 604/288.03, 6.1, 247, 99.04, 246, 256
See application file for complete search history.

(56) References Cited

U.S. PATENT DOCUMENTS

| | | | |
|---|---|---|---|
| 4,197,848 A | 4/1980 | Garrett et al. | |
| 4,535,819 A | 8/1985 | Atkinson et al. | |
| 4,692,146 A | 9/1987 | Hilger | |
| 4,765,588 A | 8/1988 | Atkinson | |
| 4,915,687 A * | 4/1990 | Sivert ............ | 604/83 |
| 4,934,655 A | 6/1990 | Blenkush et al. | |
| 4,953,594 A | 9/1990 | Von Berg | |
| 5,006,114 A | 4/1991 | Rogers et al. | |
| 5,049,128 A | 9/1991 | Duquette | |
| 5,065,783 A | 11/1991 | Ogle, II | |
| 5,104,389 A | 4/1992 | Deem et al. | |
| 5,108,380 A | 4/1992 | Herlitze et al. | |
| 5,147,333 A * | 9/1992 | Raines ............ | 604/249 |
| 5,163,922 A | 11/1992 | McElveen, Jr. et al. | |
| 5,203,775 A * | 4/1993 | Frank et al. ............ | 604/256 |
| 5,230,706 A | 7/1993 | Duquette | |
| 5,242,393 A | 9/1993 | Brimhall et al. | |
| 5,242,423 A | 9/1993 | Goodsir et al. | |
| 5,242,432 A | 9/1993 | DeFrank | |
| 5,251,873 A | 10/1993 | Atkinson et al. | |
| 5,261,895 A | 11/1993 | Kablik | |
| 5,269,771 A | 12/1993 | Thomas et al. | |
| 5,281,206 A | 1/1994 | Lopez | |
| 5,289,849 A | 3/1994 | Paradis | |
| 5,330,450 A | 7/1994 | Lopez | |
| 5,344,414 A | 9/1994 | Lopez et al. | |
| 5,353,837 A | 10/1994 | Faust | |
| 5,360,413 A * | 11/1994 | Leason et al. ............ | 604/249 |
| 5,380,306 A | 1/1995 | Brinon | |
| 5,390,898 A | 2/1995 | Smedley et al. | |
| 5,395,348 A | 3/1995 | Ryan | |
| 5,401,245 A | 3/1995 | Haining | |
| 5,423,791 A | 6/1995 | Bartlett | |
| 5,425,465 A | 6/1995 | Healy | |
| 5,439,451 A | 8/1995 | Collinson et al. | |
| 5,441,487 A | 8/1995 | Vedder | |
| 5,462,255 A * | 10/1995 | Rosen et al. ............ | 251/149.6 |
| 5,466,219 A | 11/1995 | Lynn et al. | |

(Continued)

Primary Examiner — Nicholas Lucchesi
Assistant Examiner — Quynh-Nhu H Vu
(74) Attorney, Agent, or Firm — Klein, O'Neill & Singh, LLP

(57) ABSTRACT

Needleless access port valves are generally discussed herein with particular discussions extended to needleless access port valves having a pliant valve housing interacting with an inlet connector assembly. The pliant valve housing has an integrally formed valve stem and one or more ports. The valve stem cooperates with a nozzle on the inlet connector assembly to form a slip port, which can open when exerted by force to permit flow or closes when the force is removed.

22 Claims, 8 Drawing Sheets

U.S. PATENT DOCUMENTS

| | | | |
|---|---|---|---|
| 5,509,433 A | 4/1996 | Paradis | |
| 5,509,912 A | 4/1996 | Vaillancourt et al. | |
| 5,533,983 A | 7/1996 | Haining | |
| 5,535,771 A | 7/1996 | Purdy et al. | |
| 5,535,785 A | 7/1996 | Werge et al. | |
| 5,540,661 A | 7/1996 | Tomisaka et al. | |
| 5,549,577 A | 8/1996 | Siegel et al. | |
| 5,569,235 A | 10/1996 | Ross et al. | |
| 5,573,516 A | 11/1996 | Tyner | |
| 5,584,808 A | 12/1996 | Healy | |
| 5,616,129 A | 4/1997 | Mayer | |
| 5,620,434 A | 4/1997 | Brony | |
| 5,624,414 A | 4/1997 | Boettger | |
| 5,645,538 A | 7/1997 | Richmond | |
| 5,674,206 A | 10/1997 | Allton et al. | |
| 5,676,346 A | 10/1997 | Leinsing | |
| 5,685,866 A | 11/1997 | Lopez | |
| 5,690,612 A | 11/1997 | Lopez et al. | |
| 5,694,686 A | 12/1997 | Lopez | |
| 5,695,466 A | 12/1997 | Lopez et al. | |
| 5,699,821 A | 12/1997 | Paradis | |
| 5,700,248 A | 12/1997 | Lopez | |
| 5,730,418 A * | 3/1998 | Feith et al. | 251/149.6 |
| 5,738,663 A | 4/1998 | Lopez | |
| 5,741,228 A | 4/1998 | Lambrecht et al. | |
| 5,743,894 A | 4/1998 | Swisher | |
| 5,776,113 A | 7/1998 | Daugherty et al. | |
| 5,782,816 A | 7/1998 | Werschmidt et al. | |
| 5,785,693 A | 7/1998 | Haining | |
| 5,788,215 A | 8/1998 | Ryan | |
| 5,806,551 A | 9/1998 | Meloul et al. | |
| 5,806,831 A | 9/1998 | Paradis | |
| 5,810,768 A | 9/1998 | Lopez | |
| 5,810,792 A | 9/1998 | Fangrow, Jr. et al. | |
| 5,810,793 A | 9/1998 | Boettger | |
| 5,839,715 A | 11/1998 | Leinsing | |
| 5,848,994 A | 12/1998 | Richmond | |
| 5,873,862 A | 2/1999 | Lopez | |
| 5,901,942 A | 5/1999 | Lopez | |
| 5,921,264 A | 7/1999 | Paradis | |
| 5,921,419 A | 7/1999 | Niedospial, Jr. et al. | |
| 5,928,204 A | 7/1999 | Lopez | |
| 5,957,898 A | 9/1999 | Jepson et al. | |
| 5,967,490 A | 10/1999 | Pike | |
| 5,971,950 A | 10/1999 | Lopez et al. | |
| 5,980,741 A * | 11/1999 | Schnell et al. | 210/188 |
| 6,019,748 A | 2/2000 | Lopez | |
| 6,029,946 A | 2/2000 | Doyle | |
| 6,036,171 A | 3/2000 | Weinheimer et al. | |
| 6,039,302 A | 3/2000 | Cote, Sr. et al. | |
| 6,045,534 A | 4/2000 | Jacobsen et al. | |
| 6,063,062 A | 5/2000 | Paradis | |
| 6,068,011 A | 5/2000 | Paradis | |
| 6,083,194 A | 7/2000 | Lopez | |
| 6,106,502 A | 8/2000 | Richmond | |
| 6,113,068 A | 9/2000 | Ryan | |
| 6,117,114 A | 9/2000 | Paradis | |
| 6,127,320 A | 10/2000 | van Ooij et al. | |
| 6,132,403 A | 10/2000 | Lopez | |
| 6,132,404 A | 10/2000 | Lopez | |
| 6,142,446 A | 11/2000 | Leinsing | |
| 6,168,137 B1 | 1/2001 | Paradis | |
| 6,170,800 B1 | 1/2001 | Meloul et al. | |
| 6,171,287 B1 | 1/2001 | Lynn et al. | |
| 6,189,859 B1 | 2/2001 | Rohrbough et al. | |
| 6,221,065 B1 | 4/2001 | Davis | |
| 6,228,069 B1 | 5/2001 | Barth et al. | |
| 6,245,048 B1 | 6/2001 | Fangrow, Jr. et al. | |
| 6,245,056 B1 | 6/2001 | Walker et al. | |
| 6,261,282 B1 | 7/2001 | Jepson et al. | |
| 6,273,869 B1 | 8/2001 | Vaillancourt | |
| 6,290,206 B1 | 9/2001 | Doyle | |
| 6,290,688 B1 | 9/2001 | Lopez et al. | |
| 6,299,131 B1 | 10/2001 | Ryan | |
| 6,299,132 B1 | 10/2001 | Weinheimer et al. | |
| 6,325,782 B1 | 12/2001 | Lopez | |
| 6,344,033 B1 | 2/2002 | Jepson et al. | |
| 6,364,869 B1 | 4/2002 | Bonaldo | |
| 6,428,520 B1 | 8/2002 | Lopez et al. | |
| 6,482,188 B1 | 11/2002 | Rogers et al. | |
| 6,491,668 B1 | 12/2002 | Paradis | |
| 6,541,802 B2 | 4/2003 | Doyle | |
| 6,572,592 B1 | 6/2003 | Lopez | |
| 6,585,229 B2 | 7/2003 | Cote, Sr. et al. | |
| 6,599,273 B1 | 7/2003 | Lopez | |
| 6,616,627 B2 | 9/2003 | Willis et al. | |
| 6,626,418 B2 | 9/2003 | Kiehne | |
| 6,635,044 B2 | 10/2003 | Lopez | |
| 6,641,561 B1 | 11/2003 | Hill et al. | |
| 6,645,170 B2 | 11/2003 | Landau | |
| 6,669,673 B2 | 12/2003 | Lopez | |
| 6,669,681 B2 | 12/2003 | Jepson et al. | |
| 6,682,509 B2 | 1/2004 | Lopez | |
| 6,695,817 B1 | 2/2004 | Fangrow, Jr. | |
| 6,706,022 B1 | 3/2004 | Leinsing et al. | |
| 6,755,391 B2 | 6/2004 | Newton et al. | |
| 6,758,833 B2 | 7/2004 | Lopez | |
| 6,802,490 B2 | 10/2004 | Leinsing et al. | |
| 6,840,501 B2 | 1/2005 | Doyle | |
| 6,855,138 B2 | 2/2005 | Tsai | |
| 6,869,426 B2 | 3/2005 | Ganem | |
| 6,871,838 B2 | 3/2005 | Raines et al. | |

* cited by examiner

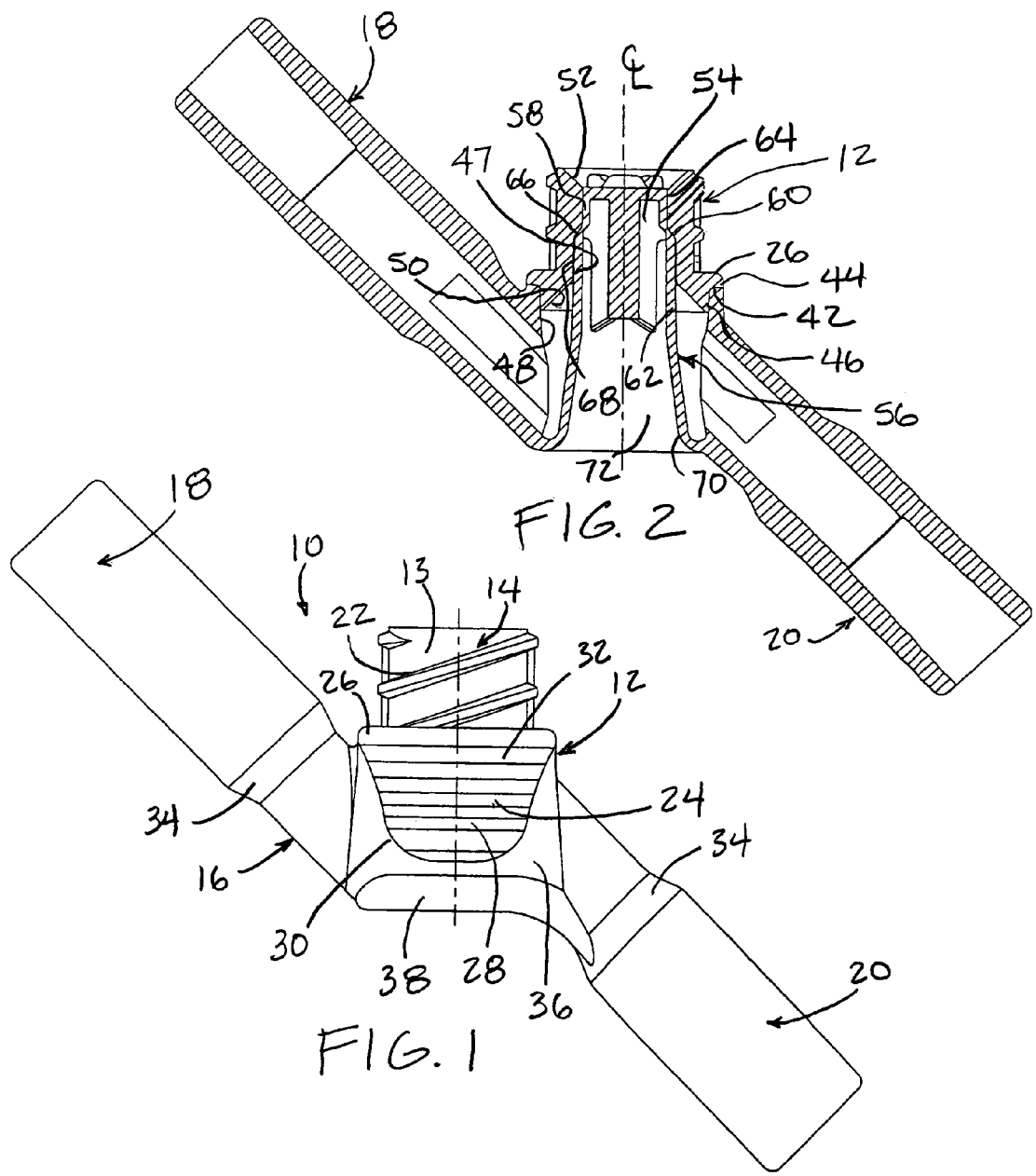

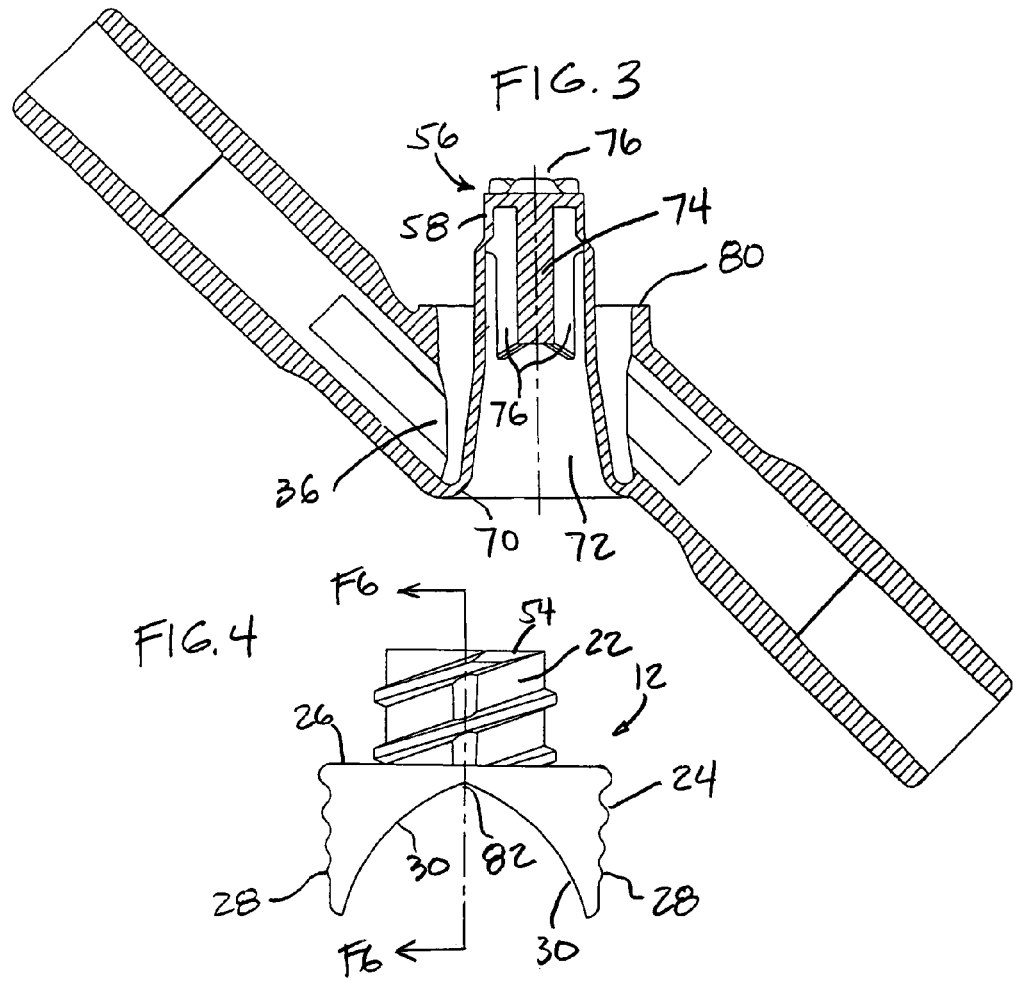
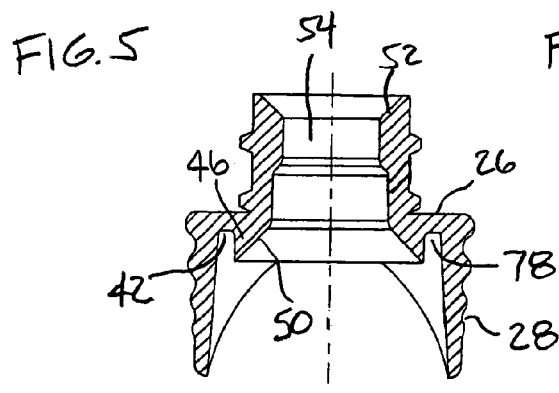
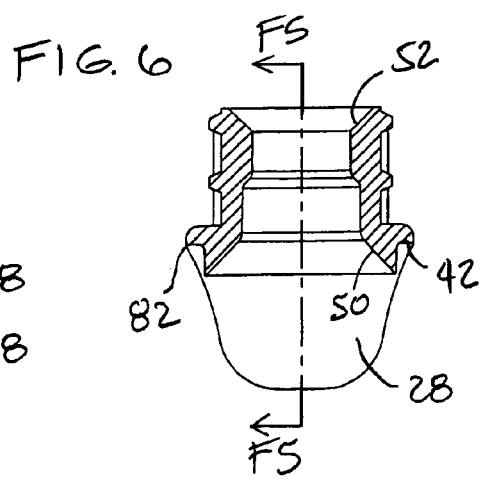

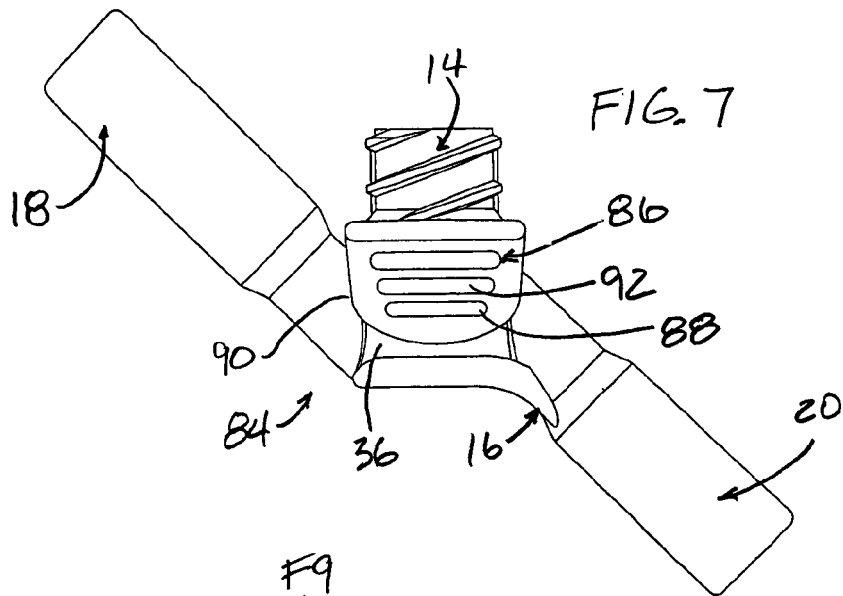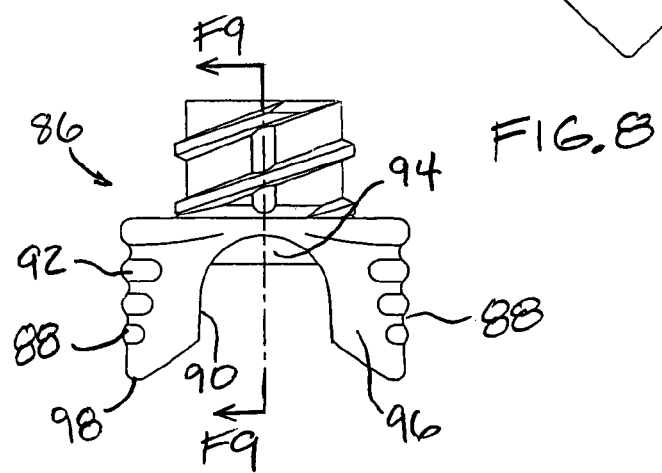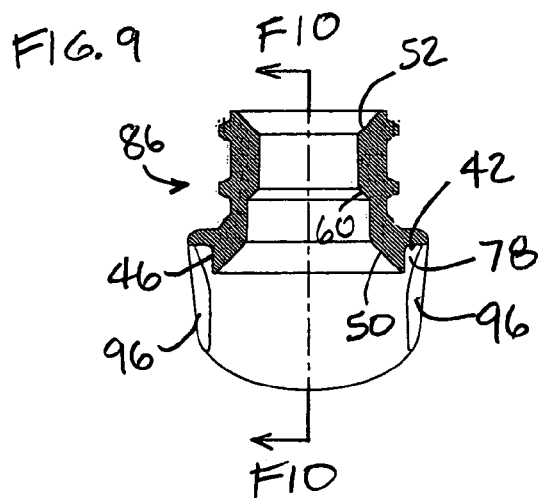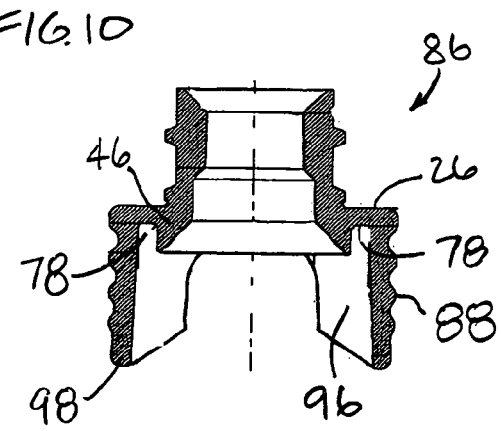

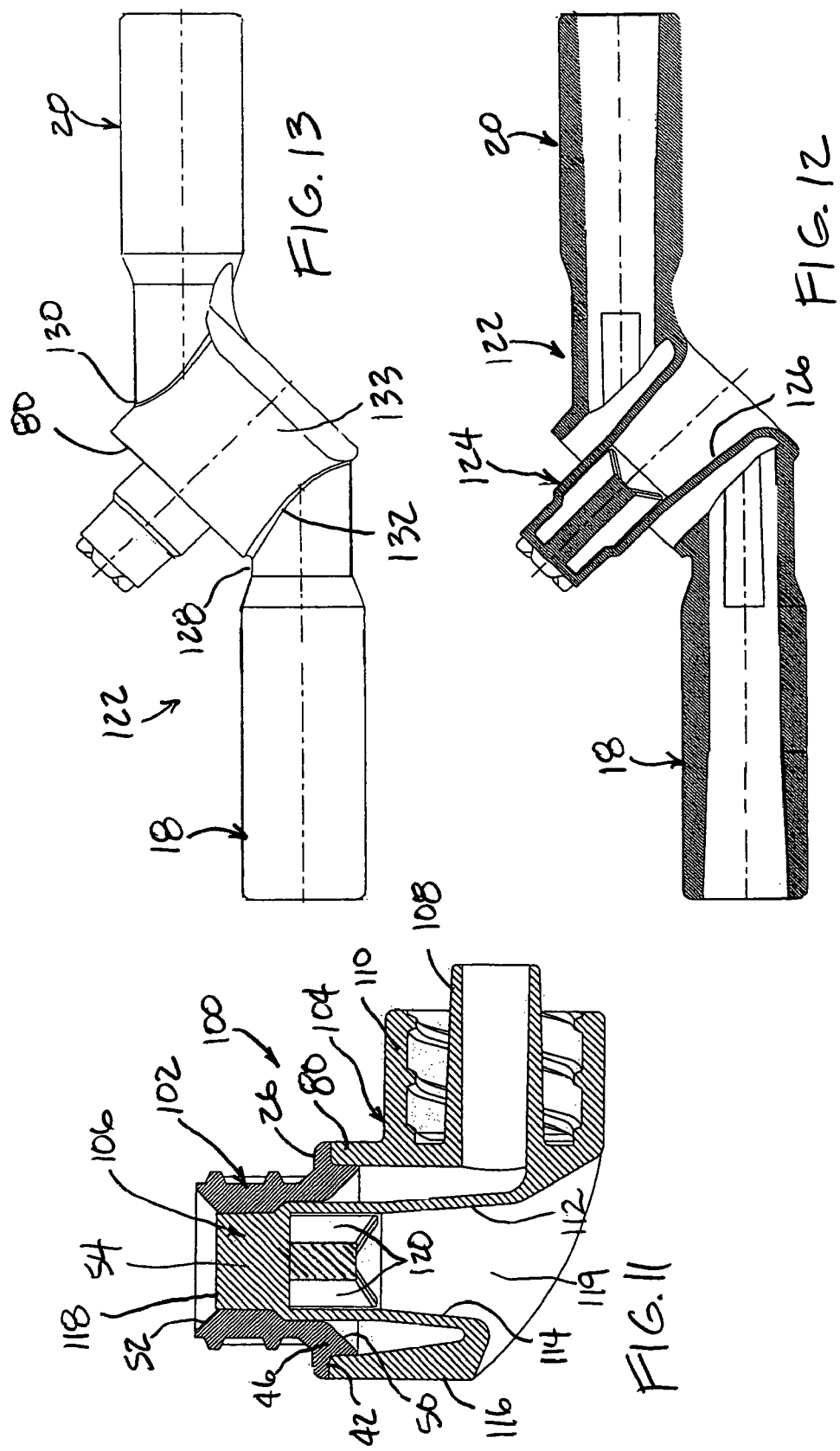

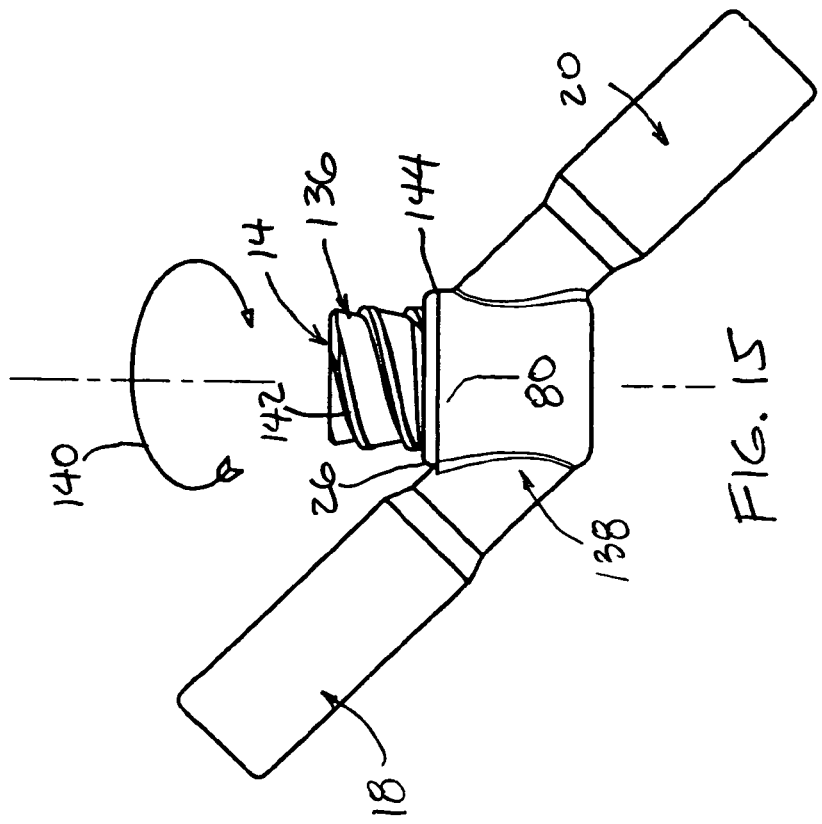
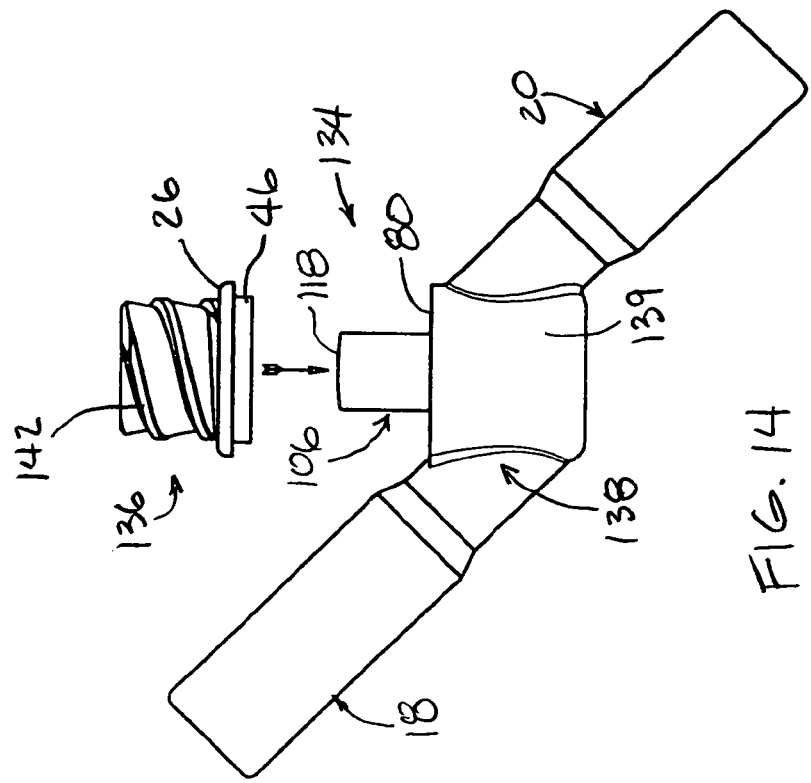

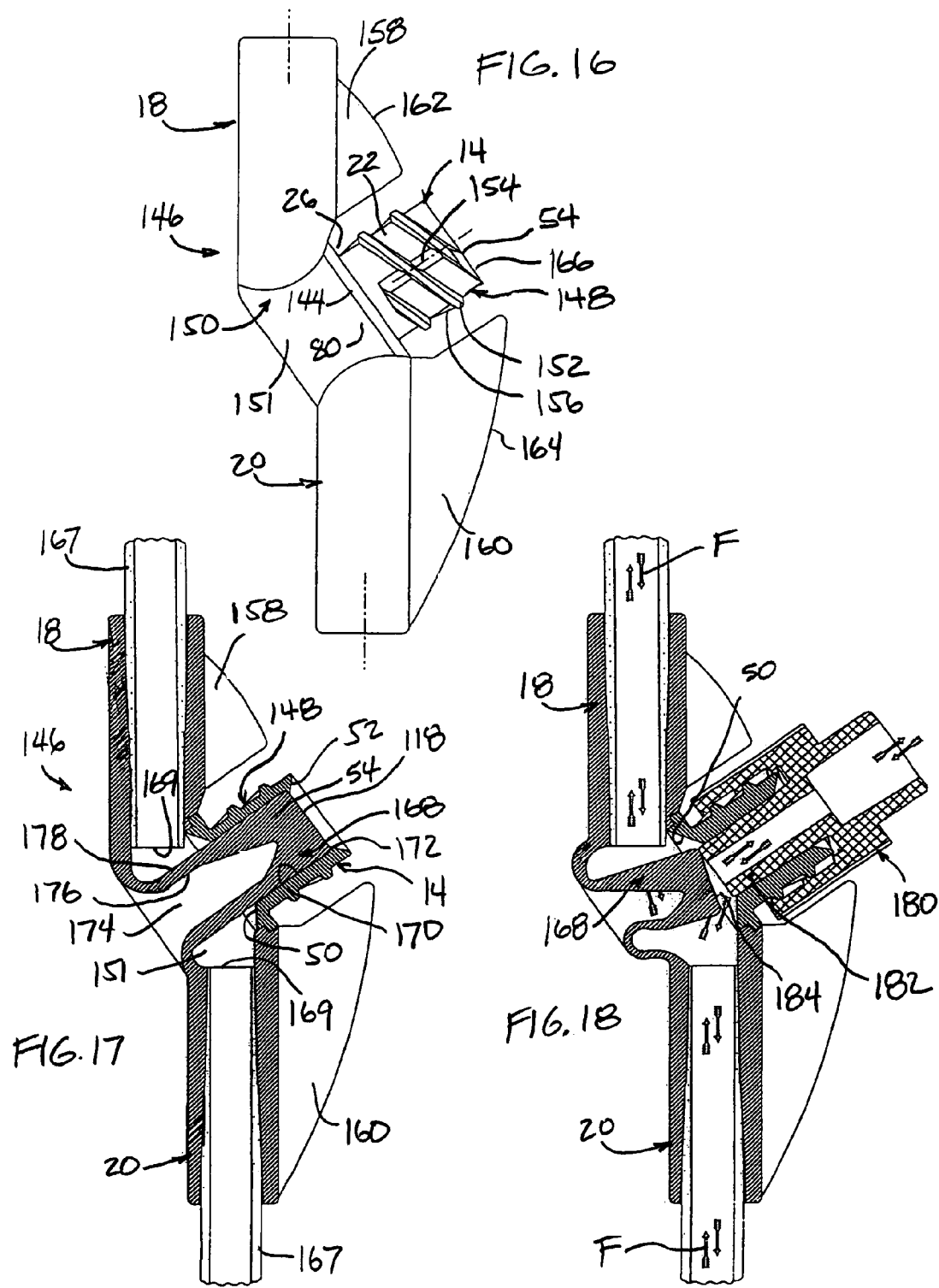

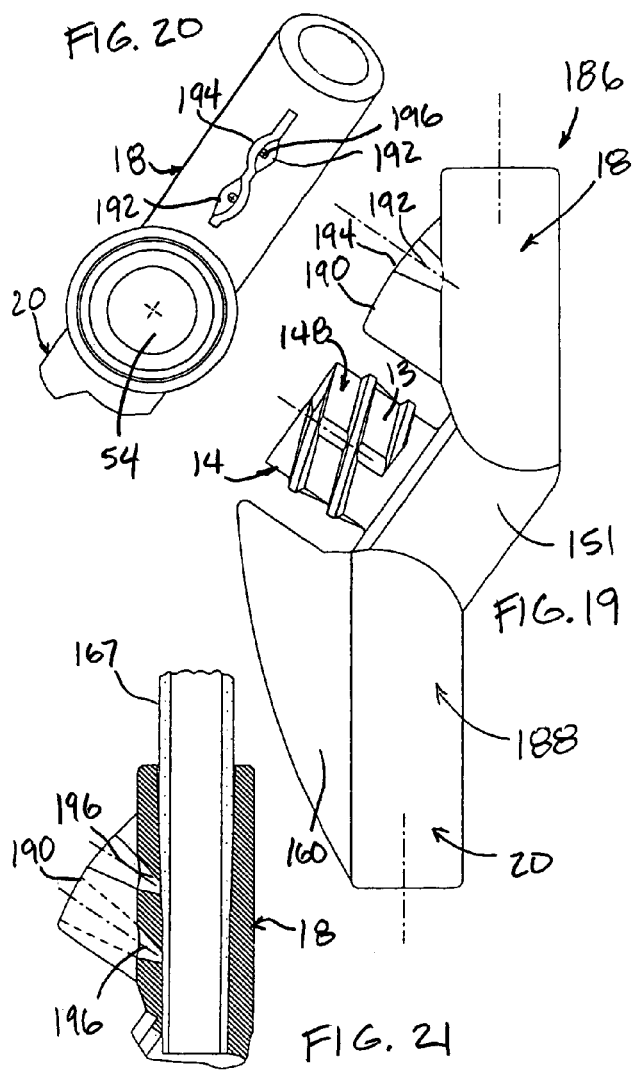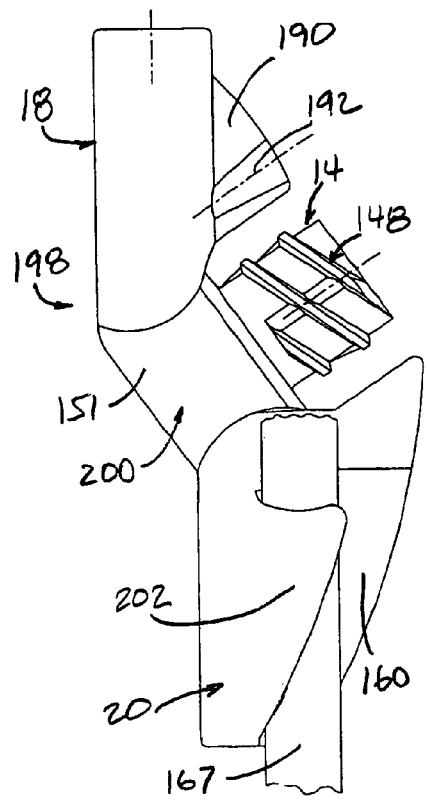

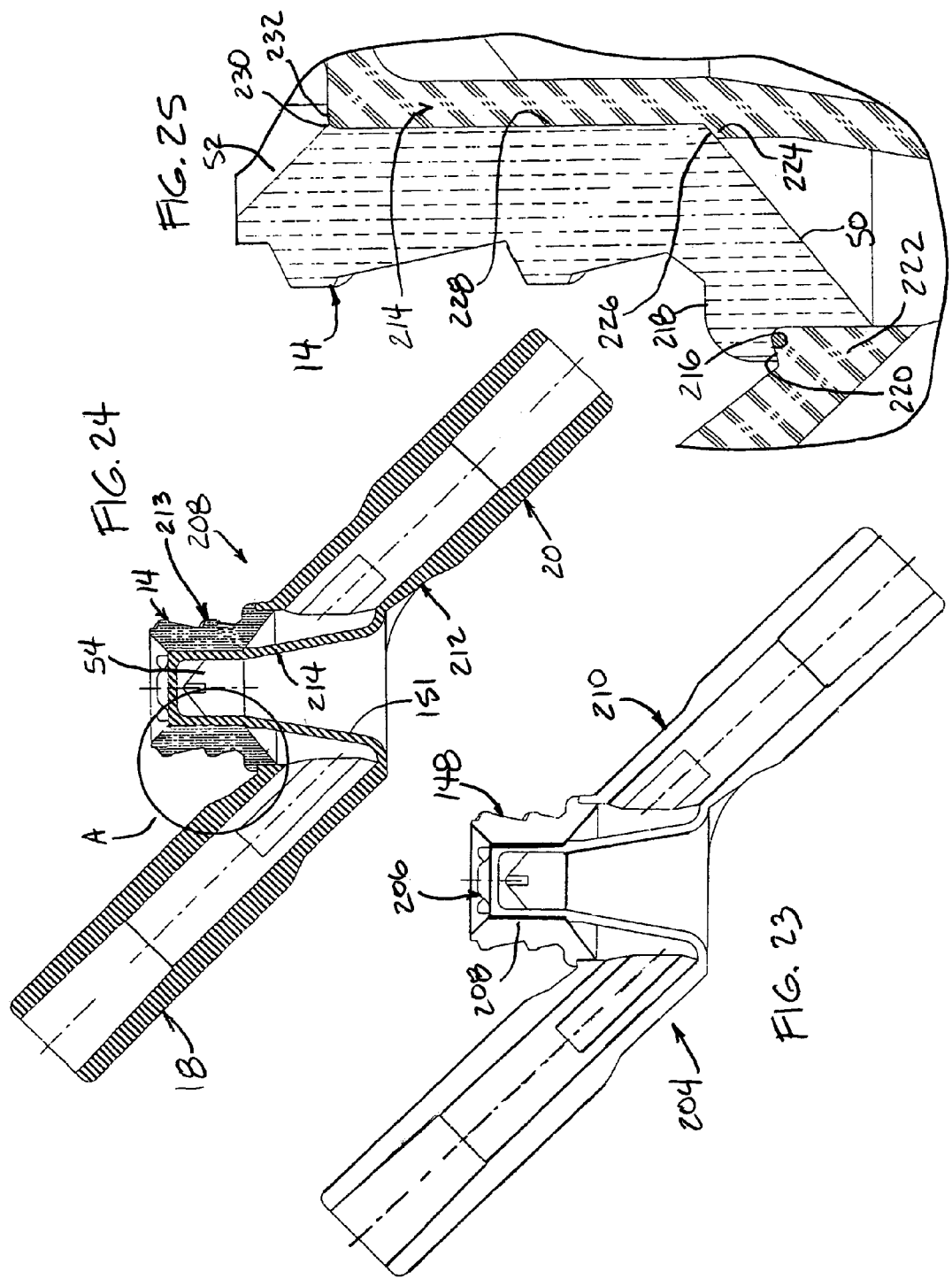

NEEDLELESS ACCESS PORT VALVES

Needleless access port valves are generally discussed herein with particular discussions extended to needleless access port valves comprising a pliant valve housing interacting with a nozzle of a port.

BACKGROUND

Needleless access port valves are widely used in the medical industry for accessing an IV line and/or the internals of a patient or subject. Generally speaking, prior art valves utilize a valve housing in combination with a moveable internal plug or piston to control the flow of fluid through a valve. The plug or piston may be moved by a syringe or a medical implement to open the inlet of the valve for accessing the interior cavity of the valve. When a fluid is delivered through the valve, fluid flow typically flows around the outside of the plug or piston in the direction towards the outlet. Upon removal of the syringe or medical implement, the plug or piston returns to its original position, either un-aided or aided by a biasing means, such as a spring or a diaphragm.

In some prior art valves, when the syringe or medical implement pushes the plug or piston, the plug or piston is pierced by a piercing device, such as a spike. The spike typically incorporates one or more fluid channels for fluid flow flowing through the pierced piston and then through the fluid channels in the spike. In yet other prior art valves, a self-flushing or positive flush feature is incorporated to push residual fluids confined inside the interior cavity of the valve to flow out the outlet when the syringe or medical implement is removed.

While prior art needleless access port valves are viable options for their intended applications, there remains a need for alternative needleless access port valves.

SUMMARY

The present invention may be implemented by providing a needleless injection port valve comprising an inlet connector assembly comprising a nozzle comprising an inlet lumen; a valve housing comprising at least one port and an integrally molded valve stem positioned at an angle to the at least one port; the valve stem comprising a hollow interior cavity in constant fluid communication with ambient air; wherein the inlet connector assembly is secured to the valve housing and the valve stem projects, at least in part, through the inlet lumen of the inlet connector assembly.

In yet another aspect of the present invention, there is provided a needleless injection port valve comprising an inlet connector assembly comprising a nozzle comprising an inlet lumen; a valve housing comprising at least one port and an integrally molded valve stem positioned at an angle to the at least one port; the valve stem comprising a hollow interior cavity and at least one rib positioned in the hollow interior cavity for reinforcing a section of the valve stem; wherein the valve stem projects, at least in part, through the inlet lumen of the inlet connector assembly and the inlet connector assembly is secured to the valve housing along a sealing seam.

The present invention also includes various methods for supplying fluid through needleless injection port valves including a method comprising the steps of (1) providing a valve, the valve comprising: (a) an inlet connector assembly comprising a nozzle comprising an inlet lumen; (b) a valve housing comprising at least one port and an integrally molded valve stem positioned at an angle to the at least one port; the valve stem comprising a hollow interior cavity and a rib positioned in the hollow interior cavity for reinforcing a section of the valve stem; (c) the valve stem projects, at least in part, through the inlet lumen of the inlet connector assembly and the inlet connector assembly is secured to the valve housing along a sealing seam; (2) inserting a male end of a medical implement through the inlet lumen of the inlet connector assembly; and (3) injecting fluid from the medical implement through the inlet lumen.

Other aspects and variations of the valve assemblies summarized above are also contemplated and will be more fully understood when considered with respect to the following disclosure.

BRIEF DESCRIPTION OF THE DRAWINGS

These and other features and advantages of the present invention will become appreciated as the same become better understood with reference to the specification, claims and appended drawings wherein:

FIG. 1 is a semi-schematic side view of a Y-site valve provided in accordance with aspects of the present invention;

FIG. 2 is a semi-schematic cross-sectional side view of the valve of FIG. 1 in a first position;

FIG. 3 is a semi-schematic cross-sectional side view of the valve of FIG. 1 without the inlet connector assembly for clarity;

FIG. 4 is a semi-schematic side view of the inlet connector assembly of FIG. 1;

FIG. 5 is a semi-schematic cross-sectional view of the inlet connector assembly of FIG. 4 taken along line F5-F5 of FIG. 6;

FIG. 6 is a semi-schematic cross-sectional view of the inlet connector assembly of FIG. 4 taken along line F6-F6;

FIG. 7 is a semi-schematic side view of an alternative valve embodiment provided in accordance with aspects of the present invention;

FIG. 8 is a semi-schematic side view of the inlet connector assembly of FIG. 7;

FIG. 9 is a semi-schematic cross-sectional view of the inlet connector assembly of FIG. 8 taken along line F9-F9;

FIG. 10 is a semi-schematic cross-sectional view of the inlet connector assembly of FIG. 8 taken along line F10-F10 of FIG. 9;

FIG. 11 is a semi-schematic cross-sectional side view of yet another alternative valve embodiment provided in accordance with aspects of the present invention;

FIG. 12 is a semi-schematic cross-sectional side view of still yet another alternative valve embodiment provided in accordance with aspects of the present invention;

FIG. 13 is a semi-schematic side view of the valve of FIG. 12;

FIG. 14 is a semi-schematic exploded side view of still yet another alternative valve embodiment provided in accordance with aspects of the present invention;

FIG. 15 is a semi-schematic side view of the valve of FIG. 14;

FIG. 16 is a semi-schematic side view of yet another alternative injection port valve embodiment provided in accordance with aspects of the present invention;

FIG. 17 is a semi-schematic cross-sectional side view of the valve of FIG. 16 in a first position and having tubes connected to the first and second ports;

FIG. 18 is a semi-schematic cross-sectional side view of the valve of FIG. 16 in a second position having a medical implement engaged to the inlet or slip port;

FIG. 19 is a semi-schematic side view of yet another valve embodiment provided in accordance with aspects of the present invention comprising one or more emergency access ports;

FIG. 20 is a semi-schematic partial perspective view of the valve of FIG. 19 from a different viewing plane;

FIG. 21 is a semi-schematic partial cross-sectional view of the valve of FIG. 19;

FIG. 22 is a semi-schematic side view of still yet another alternative valve embodiment provided in accordance with aspects of the present invention;

FIG. 23 is a semi-schematic cross-sectional side view of still yet another valve embodiment provided in accordance with aspects of the present invention;

FIG. 24 is a semi-schematic cross-sectional side view of yet another injection port valve embodiment provided in accordance with aspects of the present invention; and FIG. 25 is a semi-schematic partial cross-sectional view of the valve of FIG. 24, which is a blown-up view of section A.

DETAILED DESCRIPTION

The detailed description set forth below in connection with the appended drawings is intended as a description of the presently preferred embodiments of needleless access port valves or backcheck valves (herein "valves") provided in accordance with aspects of the present invention and is not intended to represent the only forms in which the present invention may be constructed or utilized. The description sets forth the features and the steps for constructing and using the valves of the present invention in connection with the illustrated embodiments. It is to be understood, however, that the same or equivalent functions and structures may be accomplished by different embodiments that are also intended to be encompassed within the spirit and scope of the invention. As denoted elsewhere herein, like element numbers are intended to indicate like or similar elements or features.

Referring now to FIG. 1, a semi-schematic side view of a first exemplary needleless access or injection port valve provided in accordance with aspects of the present invention is shown, which is generally designated 10. The needleless access port valve 10 (herein "valve") comprises an inlet connector assembly 12 comprising a nozzle 13 configured to cooperate with a plug or stem 56 (FIG. 2) to form an inlet or slip port 14. The connector assembly 12 is fixedly secured to a valve housing 16 comprising a first port or first inlet port 18 and a second port 20. The valve 10 may be referred to as a Y-site or a 3-way injection port valve in that fluid may flow through the valve via three different ports 14, 18, 20. In one exemplary embodiment, the valve 10 may be connected to an IV set by inserting a tube (not shown) in the first inlet port 18 and a second tube (not shown) in the second port 20 and allowing medications to be administered through the second inlet port or slip port 14 via a medical implement, such as a syringe. The valve 10 may also be used as a connection point for a piggyback and for other applications known in the medical field.

In one aspect of the present invention, the valve 10 may be manufactured by assembling the inlet connector assembly 12 to the valve housing 16 and welding the two together to form a sealed interface. The inlet connector assembly 12 may be made from a rigid or semi-rigid plastic of a semi-crystalline polymer type, such as polycarbonate, polypropylene, polyethylene, and nylon and more preferably from an elastomeric plastic of a thermoplastic elastomer (TPE) type such as the copolyamide (COPA) family of thermoplastic elastomers. In a preferred embodiment, the COPA is copolyamide thermoplastic elastomer having a commercial trade name PEBAX®. However, other TPEs may also be used to make the inlet connector assembly 12, including thermoplastic polyurethanes (TPUs), styrenic thermoplastic elastomers, thermoplastic polyolefins (TPOs), copolyesters (COPEs), and thermoplastic vulcanizate elastomeric alloys (TPVs). Optionally, the TPEs may be cross-linked either chemically or by irradiation to alter their characteristics. The connector assembly 12 comprises a female luer taper with a female luer lock 22 and a connecting stem 24. The connecting stem 24 is configured to mate with a bonnet or collar on the valve housing 16 and comprises a flange 26, a pair of connecting shells 28, and a sealing edge 30 for sealing engagement with the valve housing, as further discussed below. A plurality of gripping surfaces 32 may optionally be incorporated on the exterior surface of the shells 28 to facilitate gripping the valve 10.

In one exemplary embodiment, the valve housing 16 is integrally molded from a TPE material. More preferably, the TPE is similar to the TPE used to make the inlet connector assembly 12. Alternatively, polycarbonate may be used to make the inlet connector assembly 12. The integrally formed valve housing 16 comprises the two ports 18, 20, a valve body 36, and a valve stem or plug 56 (FIG. 2). The integrally molded first port 18 and second port 20 are preferably formed with universal tubing configuration and comprises a female luer for receiving tubing from an IV set or the like. A reduced section 34 immediately adjacent each port may be included for aesthetic appeal but may otherwise optionally be excluded. Other aesthetic features may be included such as providing the valve with one or more colors and incorporating curves and contours for design appeal, such as including a tapered end section 38 at the base of the valve body 36, which also provides a gripping point.

In addition to providing a gripping surface 32, the shells 28 straddle the valve body 16 and are positioned in between the two ports 18, 20. Thus, the shells 28 serve to angularly align the inlet connector assembly 12 relative to the valve body 16. The relative orientation also allows the threads on the female luer lock 22 to be engaged at a predetermined angle, if desired.

FIG. 2 is a semi-schematic cross-sectional view of the valve 10 of FIG. 1. As shown, the flange 26 comprises a seat 42 abutting the seat 44 of the valve body 16. A collar 46 extends from the seat 42 and matingly engages the interior surface 48 of the valve body 16 preferably in an interference engagement of about 0.5-2 mils total interference. To facilitate assembly, both the collar 46 and the interior surface 48 of the valve body 16 incorporate a tapered surface. The interface between the two seats 42, 44 may be welded or glued to firmly secure the inlet connector assembly 12 to the valve body 16.

A tapered or beveled return guide 50 and a tapered or beveled inlet guide 52 are incorporated in the inlet connector assembly 12. As is readily apparent to a person of ordinary skill in the art, the beveled inlet guide 52 facilitates insertion of a male medical implement (not shown) by guiding the medical implement towards the opening 54 of the second inlet or slip port 14. Similarly, the beveled return guide 50 assists the valve stem 56 in returning to its first position, which closes the opening 54 of the slip port 14 and prevents flow flowing therethrough. The valve stem or plug 56 closes the opening 54 by forming a fluid tight seal with the interior cavity or lumen of the inlet nozzle 13. The fluid tight seal is provided by corresponding mating surfaces of the valve stem 56 and the interior surface 47 of the nozzle 13. In one exemplary embodiment, the valve stem 56 comprises an upper stem section 58, a neck 60, and a stem base 62. The various stem sections are adapted to abut an upper inlet section 64, a neck 66, and an inlet base 68 of the inlet connector assembly 12 to form a fluid-tight seal. In a preferred embodiment, the mating surfaces are tapered and the fluid tight seal is provided by biasing the stem 56 in the direction of the opening 54 to create a compressed surface-to-surface contact against the interior surface 47 of the nozzle 13. Although an external biasing force, such as a spring or a resilient disc or diaphragm, could be incorporated to bias the valve stem in the direction of the opening 54, in a preferred embodiment, the stem is configured to be self-biasing. The self-biasing characteristic of the valve stem is derived, at least in part, from the resilient and flexible material used to form the valve housing, and hence the valve stem.

Referring now to FIG. 3, a semi-schematic cross-sectional side view of the valve housing 16 without the inlet connector assembly 12 is shown. In one exemplary embodiment, the valve stem 56 is integrally molded to the valve body 36 and comprises a curvilinear base 70, which curves inwardly in the direction of the interior cavity 72 of the valve stem. When the valve stem 56 is deflected, the curvilinear base 70 operates to return the valve stem back to its first position as shown. A post or a rib 74 is incorporated and is adapted to stiffen the upper stem section 58 of the stem 56 to enable the stem to receive a load from a medical implement. In one exemplary embodiment, the rib 74 is integrally molded to the stem 56 and is formed by including three spaced apart mold release chambers 76, which are preferably equally spaced apart. One or more top projections 76 on the top surface of the stem 56 may be incorporated. The projections 76 create crevices and channels for fluid flow flowing from or towards a medical implement.

Turning now to FIGS. 4, 5, and 6, different views of the inlet connector assembly 12 are shown. FIG. 5 is a cross-sectional view of FIG. 6 taken along line F5-F5 while FIG. 6 is a cross-sectional view of FIG. 4 taken along line F6-F6. As shown in FIG. 4, two shoulders 82 formed between the two connecting shells 28 are configured to straddle the first and second ports 18, 20 when the inlet connector assembly 12 is mounted over the valve body 16 (FIG. 1). Interiorly, a tip retaining gap 78 (FIG. 5) is formed between the collar 46 and the two shells 28. In one exemplary embodiment, the retaining gap 78 is sized to receive the opening collar 80 of the valve body 36 (FIG. 3). However, the opening collar 80 of the valve body 36 merely rests against the seat 42 of the flange 36 at the apex of the shoulders 82 (FIG. 6) without being enclosed by the retaining gap 78.

Referring again to FIG. 1, after the inlet connector assembly 12 is mounted over the valve body 16, the two components may be fixedly secured to one another by bonding the interface between the seat 42 on the flange 26 and the seat 44 on the valve body 36. Alternatively or in addition thereto, the two components may be fixedly secured to one another by bonding the two along the sealing edge 30, which comprises the edge of the two shells 28 and the two shoulders 82. In one exemplary embodiment, the bonding process includes laser welding the two components with a diode type laser with other commercially available lasers also usable to weld the two components together. In an alternative embodiment, heat bonding and heat welding may be used to fixedly secure the two components together.

FIG. 7 is a semi-schematic side view of an alternative needleless injection port valve 84 provided in accordance with aspects of the present invention. The valve 84 is similar to the valve 10 of FIG. 1 and comprises a valve housing 16 and an inlet connector assembly 86 having a different pair of connecting shells 88. The different shells 88 have slightly different sealing edges 90 and different gripping surfaces 92 for facilitating gripping. Preferably, the two ports 18, 20 and the slip port 14 provide the same function as comparable ports on the valve 10 embodiment of FIG. 1.

FIG. 8 is a semi-schematic side view of the inlet connector assembly 86 of FIG. 7 shown without the valve housing 16. Two shoulders 94 (one shown) are formed between the two connecting shells or flaps 88 for accommodating the first and second ports 18, 20 of the valve housing 16. The shoulders 94 have curved configurations that correspond with the contour of the valve body for improved fit, assembly, alignment, and accurate sealing. Thus, the curved configurations of the shoulders 94 may differ to accommodate or mate with a valve housing 16 comprising a different contour.

FIG. 9 is a semi-schematic cross-sectional side view of the inlet connector assembly 86 of FIG. 8 taken along line F9-F9. Retaining gaps 78 appeared to be narrowed by the extensions 96 of the two connecting shells 88, which partially occlude or narrow the size of the gaps as compared to the gaps 78 shown in FIG. 5. However, the gaps 78 are preferably constant with the gaps 78 shown in FIG. 10 and the appearance of being narrowed is simply the flap extensions 96 fading while curving away from the view shown. Optionally, the size or width of the gap of the retaining gaps 78 may vary without deviating from the spirit and scope of the present invention.

FIG. 10 is a semi-schematic cross-sectional view of the inlet connector assembly of FIG. 9 taken along line F10-F10. The retaining gaps 78 shown in the present view, which are located between the collar 46 and the mid-point or central most location of the side flaps 88, are generally constant, as previously discussed.

FIG. 11 is an alternative needleless injection port valve 100 provided in accordance with aspects of the present invention. The valve 100 generally comprises an inlet connector assembly 102 and a valve housing 104 comprising an integrally molded valve stem 106 and a male luer outlet 108 comprising a luer lock 110. In one exemplary embodiment, the inlet connector assembly 102 is similar in configuration as the inlet connector assembly of FIG. 1 or FIG. 7 and comprises, among other things, a flange 26, a tapered inlet guide 52, a tapered return guide 50, a collar 46, and a seat 42. Connecting shells may also be incorporated but are not shown. The inlet connector assembly 102 cooperates with the valve housing 104 when placing the seat 42 of the connector assembly on the opening collar 80 of the valve body and sealing the two along the sealing edge (not shown) with either a laser or a heating means.

In one exemplary embodiment, the male luer outlet 108 and the valve stem 106 of the valve housing 104 are approximately at right angle to one another. However, the angle can vary between about 30 to about 150 degrees from one another with 90 degrees being more preferred.

In one exemplary embodiment, the valve stem 106 comprises a non-symmetrical valve stem base for varying the movement of the stem when actuated by a medical implement. In one embodiment, the valve stem base section 112 closes to the outlet port 108 is longer than the valve stem base section 114 closes to the valve wall 116 of the valve body 104. This non-symmetrical configuration allows the valve stem 106 to move distally from the first position (as shown) to a second position when pushed by a medical implement and tilts as it moves distally. The tilting in turn allows the flat upper surface 118 of the valve stem 106 to tilt relative to the end surface of the medical implement (not shown) to create a gap for fluid flow flowing either from the medical implement or towards the medical implement. The tilting is caused by the valve stem base sections 112, 114 reacting differently to the same force exerted on the valve stem by a medical implement.

As previously discussed, one or more ribs 120 may be incorporated in the interior cavity 119 of the valve stem to reinforce the valve stem when the same is being exerted by a medical implement.

FIG. 12 is an alternative valve housing 122 provided in accordance with aspects of the present invention. The valve housing 122 may be useable with various inlet connector assemblies discussed elsewhere herein to produce a Y-site comprising a first port 18, a second port 20, and a slip port (not shown, which is a port formed when the valve stem cooperates with a nozzle on an inlet connector assembly). In one exemplary embodiment, the first port 18 and the second port 20 each comprises an axis that is parallel to one another. In another embodiment, the first port 18 and the second port 20 each comprises an axis that is parallel and offset from one another such that they are located on two different planes. In the embodiment shown, the valve stem 124 comprises a symmetrical stem base 126 and comprises an axis that is positioned approximately 30-90 degrees from the first port and approximately 90 to 150 degrees from the second port 20. More preferably, the stem's axis is about 45 degrees from the axis of the first port 18 and about 135 degrees from the axis of the second port 20. The symmetrical stem base allows the valve stem to travel substantially uniformly or evenly when actuated by a medical implement and not substantially tilt relative to the axis defined by the valve stem. In an alternative embodiment, the stem may have a flat upper surface and the stem base be non-symmetrical such that the stem will substantially tilt when actuated by a medical implement.

FIG. 13 is a semi-schematic side view of the valve housing 122 of FIG. 12. Of notable interest is the angle 128 between the opening collar 80 and the first port 18 and the angle 130 between the opening collar and the second port 130. Also of notable interest is the curvature or configuration 132 of the valve body 133 of the valve housing 122. The angles 128, 130 and the curvature 130 of the valve body 133 should be matched with an inlet connector assembly (not shown) that has corresponding contour and curvatures to form a size-on-size fit for purposes of welding the two either with a laser or a heat source to fixedly secure the two together.

FIG. 14 is a semi-schematic exploded side view of an alternative valve embodiment 134 provided in accordance with aspects of the present invention. Similar to earlier described valves, the valve 134 shown comprises an inlet connector assembly 136 and a valve housing 138 comprising a first port 18, a second port 20, and a valve body 139 comprising a valve stem 106 comprising a flat upper surface 118. The valve 134 is a Y-site valve in that the first port 18 and the second port 20 are in constant fluid communication with one another while the second inlet port or slip port 14 (FIG. 15) is only in fluid communication with the first and second ports 18, 20 when the valve stem 106 is actuated by a medical implement (not shown).

As clearly shown in FIG. 14, the opening collar 80 of the valve body 138 is configured to abut the flange 26 and receive the collar 46 on the inlet connector assembly 136. However, unlike inlet connector assemblies discussed elsewhere herein, the present inlet connector assembly 136 does not incorporate side flaps or shoulders. Thus, the inlet connector assembly 136 is unrestrained by the geometry of the flaps and is mountable on the valve body 139 in various permissible angular orientation 140 relative to the valve body 139. Preferably, however, the threads on the inlet connector assembly 136 are positioned such that the first thread 142 is located approximately as shown so that engagement with a medical implement is initiated at a predetermined first rotation.

The inlet connector assembly 136 may be fixedly secured to the valve housing 138 by welding the two along the sealing seam 144 defined by the interface between the flange 26 and the opening collar 80. In an alternative embodiment, the valve stem 106 may incorporate projections on the top surface for providing flow channels for fluid flow from either a medical implement or towards the medical implement.

FIG. 16 is a semi-schematic side view of yet another alternative injection port valve or Y-site 146 provided in accordance with aspects of the present invention. In one exemplary embodiment, the valve 146 comprises an inlet connector assembly 148 fixedly secured to a valve housing 150 along a sealing seam 144, which is located at the interface between the flange 26 and the opening collar 80 of the valve body 151. In one embodiment, the inlet connector assembly 148 does not incorporate side flaps or connecting shells but may do so to limit the angular orientation between the connector assembly 148 and the valve housing 150. In a preferred embodiment, full exterior threads 152 and one or more ribs 154 are incorporated on the female luer lock 22. The one or more ribs 154 provide an interference fit with a medical implement. In one exemplary embodiment, the ribs 154 taper radially inwardly as they extend distally away from the inlet opening 54 of the slip port 14.

The valve housing 150, in one exemplary embodiment, comprises a first port 18 and a second port 20 each comprising an axis in a parallel and offset configuration from the other axis. The valve housing 150 is similar in construction as previously described valve housings in that it comprises the first port 18, the second port 20, the valve body 151, and a valve stem (not shown). Whereas the first and second ports 18, 20 are in constant fluid communication with one another, the slip port 14 is only in fluid communication with the first and second ports depending on the position of the valve stem (not shown). In one exemplary embodiment, the valve stem comprises a flat upper top surface and a non-symmetrical stem base. The non-symmetrical stem base allows the stem to tilt, i.e., deflect non-symmetrically, when pushed by a medical implement to create a gap between the upper top surface of the valve stem and the medical implement, as previously discussed with reference to the valve 100 of FIG. 11. However, as is readily apparent to a person of ordinary skill in the art, a stem comprising a plurality of projections on the stem upper top surface may be incorporated instead of a flat upper top surface. If incorporated, the stem base may be symmetrically formed with the valve body 151 to deflect evenly.

In one exemplary embodiment, one or more deflection ribs 158, 160 may be incorporated on the first and second ports 18, 20. In a preferred embodiment, a top deflection rib 158 comprising a top edge 162 is incorporated on the first port 18 and a bottom deflection rib 160 comprising a top edge 164 is incorporated on the second port 20. The two edges 162, 164 preferably have a contour that transitions smoothly with the top edge 166 of the slip port 14. The smooth contour allows the valve 146 to resist entanglement with other medical related instruments, such as IV lines, cables, and the like. By smooth, one edge should not extend outwardly substantially disproportionately relative to one or more other edges. In a preferred embodiment, the two fins 158, 160 are generally thin and have similar gauge or thickness as the two ports 18, 20. To further resist entanglement, gaps positioned between the slip port 14 and the deflection ribs 158, 160 are preferably smaller in dimension than the width of a typical IV line. This prevents the IV line from being trapped in between the gaps.

FIG. 17 is a semi-schematic cross-sectional side-view of the valve 146 of FIG. 16 in a first or sealed position. The valve 146 is shown with a tubing 167 frictionally engaged to the first port 18 and another tubing 167 to the second port 20. The two tube sections 167 are in fluid communication with one another through the two ports and the valve body 151, by way of fluid communication around the periphery of the valve stem 168. The length of the two ports 18, 20 and the depth in which the tube sections 167 are inserted can vary. In a preferred embodiment, the tube ends 169 do not abut or contact the plug 168 when inserted into the ports 18, 20. In the position shown, the valve stem 168 closes the opening 54 of the slip port 14 and seals the opening from fluid flow. In one exemplary embodiment, the seal is provided by urging the valve stem 168 against the interior wall surface 170 of the inlet connector assembly 148 and the stem top surface 118 against the internal lip 172 of the tapered inlet guide 52.

In one exemplary embodiment, the valve stem or plug 168 comprises a hollow interior cavity 174 comprising an interior wall surface 176 and a lengthwise axis. In a preferred embodiment, the structure of the interior wall surface 176 is non-symmetrical about the lengthwise axis. The non-symmetry is produced by providing the wall with varying thickness as measured from the exterior wall surface to the interior wall surface 176. As further discussed below with reference to FIG. 18, the non-symmetrical wall thickness allows the plug 168 to retract or move non-uniformly as it is pushed by a medical implement. The non-uniform movement of the plug 168 to a desired region within the valve body 151 can be predicted or controlled by making one side of the plug to be tilted less thick as compared to the other side(s) of the plug.

FIG. 18 is a semi-schematic cross-sectional side view of the valve 146 of FIG. 16 in a second or operative position. As shown, a medical implement 180 is threadedly engaged to the slip port 14 and the tip end 182 of the medical implement abutting the top surface 118 of the plug and pushing the plug while tilting the same. The tilting creates a gap 184 between the top surface 118 of the plug and the tip end 182 of the medical implement for fluid flow either towards the medical implement or from the medical implement.

As is well known in the art, fluid will flow in the direction of lower pressure. Thus, although the flow arrows F shown in FIG. 18 show flow flowing in two directions representing injection and aspiration, generally speaking, fluid flow will only flow in one direction at a time. Assuming, for example, the first port 18 is connected to an IV bag, the second port 20 to a catheter, and the slip port 14 to a syringe for adding a medical supplement. In this configuration, the flow of fluid will flow from the IV bag through the first port 18 towards the second port 20 and then through the catheter and inside a subject. Medication supplemented at the slip port 14 will similarly flow towards the second port 20 and mixes with the fluid from the first port 18.

When the medical implement 180 is removed from the slip port 14, the resilient material used to form the valve housing 150, and hence the valve stem 154, will no longer be restrained by the tip end 182 of the medical implement. This allows the stem 154 to recoil to its first position. In returning to its first position, the stem 154 is directed up the lumen of the slip port 14 by the tapered return guide 50.

FIG. 19 is another alternative injection port valve 186 provided in accordance with aspects of the present invention. The valve 186 is similar to the valve 146 of FIG. 16 in that it incorporates an inlet connector assembly 148 and a valve housing 188 comprising a first port 18, a second port 20, a valve body 151, and a valve stem (not shown) that cooperates with the inlet nozzle 13 of the connector assembly 148 to form a slip port 14.

Deflections ribs 160, 190 are also incorporated on the valve 186 of the present embodiment. However, in the present embodiment, the upper deflection rib 190 also functions as a guide shield for one or more emergency access ports 192. An emergency access port is a port capable of penetrating or accessing by a needle or the like for allowing the needle to be in fluid communication with the interior cavity of the valve 186. In a preferred embodiment, an emergency access port 192 is a small opening on the first port 18 that exposes the tubing 167 underneath. Alternatively, instead of an opening, a thin-wall section may be incorporated. In this alternative embodiment, the wall should be sufficiently thin so as to be penetrable by a hypodermic needle. Preferably, a curved section 194 on the deflection rib 190 is provided to guide the hypodermic needle towards the opening on the first port 18 for penetrating the tubing by the needle.

FIG. 20 is a semi-schematic partial perspective view of the valve 186 of FIG. 19. Two emergency access ports 192 are shown separated from one another by wall sections 194 of the upper deflection rib 190. Near the base of each curved wall section 194 is an opening 196 for exposing the tubing 167 underneath. The two openings 196 permit a hypodermic needle to access the interior cavity of the valve 186 and place the needle in fluid communication with the first and second ports 18, 20. FIG. 21 is a semi-schematic partial cross-sectional side view of the first port 18 of the valve 186 of FIG. 19. Clearly shown are two openings 196 on the first port 18 for exposing the tubing 167.

FIG. 22 is a semi-schematic side view of yet another alternative needleless injection port valve 198 provided in accordance with aspects of the present invention. Like other Y-site valves described elsewhere herein, the valve 198 of the present invention comprises an inlet connector assembly 148 and a valve housing 200 comprising a first port 18, a second port 20, a valve body 151, and a valve stem (not shown) cooperating with the inlet connector assembly 148 to form a second inlet port or slip port 14. The valve 198 also incorporates a lower deflection rib 160 on the second port 20 and a deflection rib 190 on the first port comprising one or more emergency access ports 192. In addition, an integrated tubing clip 202 is incorporated on the second port 20. In a preferred embodiment, the integrated tubing clip is integrally molded with the second port 20 and is sized to accommodate a tubing 167 for organizing or arranging tubings and other medical related devices. For example, the integrated clip 202 could be use to organize excess tubing length and clip adjacent tubing to prevent entanglement. Preferably, the integrated clip 202 grips the tubing 167 with a slight pressure provided by the relative dimensions of the clip and the tubing.

FIG. 23 is a semi-schematic cross-sectional side view of yet another alternative needleless injection port valve 204 provided in accordance with aspects of the present invention. The valve 204 is similar to several of the valves described elsewhere herein with one notable exception. The valve incorporates a self-lubricating material in the valve stem 206 for facilitating movement of the stem from a first position to a second position and vice versa. The self-lubricating material reduces friction between the interface of the valve stem 206 and the interior surface of the slip port 14. In one exemplary embodiment, the self-lubricating material is a two-part self-lube liquid silicone rubber. The two-part self-lube silicone rubber is commercially available from Nusil Silicone Technology of Santa Barbara, Calif. Various aspects of the self-lube liquid silicone rubber are described in Ser. No. 10/407, 001, filed Apr. 3, 2003, the contents of which are expressly incorporated herein by reference as if set forth in full. In the present embodiment, the self-lube material is co-molded over the elastomeric plastic used to make the valve housing 210, and hence the valve stem 206. As is readily apparent to a person of ordinary skill in the art, the self-lubricating material may be incorporated in any of the valve embodiments described elsewhere herein and is not construed to be limited to the valve 204 shown in FIG. 23. In another alternative embodiment, the inlet connector assembly 148 instead of or in addition to the valve stem 206 is co-molded with a self-lubricating material for reducing friction.

FIG. 24 is a semi-schematic cross-sectional view of yet another alternative valve embodiment 208 provided in accordance with aspects of the present invention. In one exemplary embodiment, the valve 208 comprises an inlet connector assembly 210 and a valve housing 212 comprising a first port 18, a second port 20, a valve body 151, and a valve stem or plug 214 that cooperates with the inlet connector assembly to form the slip port 14. As with various valve embodiments described elsewhere herein, the valve housing 212 and the inlet connector assembly 210 are preferably formed from an elastomeric plastic and are fixedly secured to one another by laser welding or use of a heating means to seal the two along a sealing seam. Also preferably, the inlet connector assembly 210 is of a shell-less type, such as that shown in, e.g., FIG. 16.

In one exemplary embodiment, the valve 208 incorporates shoulders and seats for welding and sealing purposes. Referring to FIG. 25, which is a blown-up view of section A of FIG. 24, a curve or arcuate seat 216 is incorporated on the flange 218 for mating with a corresponding arcuate seat 220 on the opening collar 222 of the valve body 151. The two arcuate seats 216, 220 enhance alignment of the inlet connector assembly 210 relative to the valve housing 212 for subsequent welding or bonding. The arcuate surfaces also provide a taper fit.

To facilitate sealing the slip port 14, the valve stem 214 incorporates a tapered seat 224 for abutting the tapered return guide 50 on the inlet connector assembly 210. In this instance, the return guide 50 functions as a shoulder 226 at the proximal end of the return guide near the transition between the return guide and the interior wall surface 228 of the inlet connector assembly.

In addition to or instead of incorporating the tapered seat 224 for sealing the slip port 14, in one exemplary embodiment, an internal sealing lip 230 is incorporated at the distal edge of the tapered inlet guide 52 near the opening 54 of the slip port 14. The plug end 232 of the plug 214 is configured to abut the internal sealing lip 230. The inherently resilient and flexible material used to form the valve housing 212, and hence the plug 214, urges the tapered seat 224 to seat against the shoulder 226 and the stem end 232 to abut the internal sealing lip 230, the latter if incorporated. In a preferred embodiment, the plug end 232 and the internal sealing lip 230 incorporate compatible curvatures for an accurate contact. As is readily apparent to a person of ordinary skill in the art, the sealing means described for the present embodiment may be incorporated in any of the valve embodiments described elsewhere herein.

Although limited embodiments of the needleless access valve assemblies and their components have been specifically described and illustrated herein, many modifications and variations will be apparent to those skilled in the art. For example, the various valves may incorporate luer-slips rather than luer threads, both the plug and the pliable valve body may be made from a two-part self-lubricating silicone rather than just the tip end section of the stem, the material selected could be opaque or semi-opaque, the various dimensions can vary, flow channels may be incorporated in the inlet lumen of the inlet connector assembly, etc. Furthermore, it is understood and contemplated that features specifically discussed for one valve embodiment may be adopted for inclusion with another valve embodiment, provided the functions are compatible. For example, the valve stem with a flat upper top surface may be incorporated in the valves currently shown and described comprising projections, the angles of various ports from the axis defined by the slip port may vary, and connecting shells may be incorporated on the inlet connector assemblies shown without the shells. Accordingly, it is to be understood that the valve assemblies and their components constructed according to principles of this invention may be embodied other than as specifically described herein. The invention is also defined in the following claims.

What is claimed is:

1. A needleless injection port valve comprising an inlet connector assembly comprising a nozzle comprising an inlet lumen; a valve housing comprising at least one port and an integrally molded valve stem positioned at an angle to the at least one port; the valve stem comprising a hollow interior cavity and at least one rib positioned in the hollow interior cavity for reinforcing a section of the valve stem; wherein the valve stem projects, at least in part, through the inlet lumen of the inlet connector assembly and the inlet connector assembly is secured to the valve housing along a sealing seam.

2. The needleless injection port valve of claim 1, wherein the valve housing comprises a second port.

3. The needleless injection port valve of claim 1, wherein the valve housing is made from a thermoplastic elastomer (TPE) material.

4. The needleless injection port valve of claim 1, wherein the hollow interior cavity is in constant fluid communication with ambient air.

5. The needleless injection port valve of claim 1, further comprising a curvilinear base disposed in between the valve stem and the valve housing.

6. The needleless injection port valve of claim 5, wherein the curvilinear base bulges outwardly when the valve stem moves from a first position to a second position.

7. The needleless injection port valve of claim 1, wherein the inlet connector assembly is made from a plastic material.

8. The needleless injection port valve of claim 7, wherein the plastic is polycarbonate.

9. The needleless injection port valve of claim 1, wherein the integrally molded valve stem comprises a generally flat upper surface.

10. The needleless injection port valve of claim 1, wherein the integrally molded valve stem comprises a top surface having a plurality of protrusions defining flow paths.

11. The needleless injection port valve of claim 1, wherein the inlet connector assembly is welded to the valve housing.

12. The needleless injection port valve of claim 1, wherein the inlet connector assembly comprises a return guide.

13. The needleless injection port valve of claim 1, wherein the return guide comprises a tapered surface.

14. The needleless injection port valve of claim 2, further comprising a deflection rib positioned on an exterior surface of the at least one port and of the second port.

15. The needleless injection port valve of claim 2, further comprising an emergency access port located on at least one of the second port or the at least one port.

16. The needleless injection port valve of claim 1, further comprising a shoulder positioned in the inlet lumen of the nozzle.

17. The needleless injection port valve of claim 1, further comprising flow channels in the inlet lumen of the nozzle.

18. The needleless injection port valve of claim 1, wherein the inlet connector assembly is welded to the valve housing along the sealing seam.

19. A method for supplying fluid through a needleless injection port valve comprising:
(1) providing a valve, the valve comprising:
 (a) an inlet connector assembly comprising a nozzle comprising an inlet lumen;
 (b) a valve housing comprising at least one port and an integrally molded valve stem positioned at an angle to the at least one port; the valve stem comprising a hollow interior cavity and a rib positioned in the hollow interior cavity for reinforcing a section of the valve stem;
 (c) the valve stem projects, at least in part, through the inlet lumen of the inlet connector assembly and the inlet connector assembly is secured to the valve housing along a sealing seam;
(2) inserting a male end of a medical implement through the inlet lumen of the inlet connector assembly; and
(3) injecting fluid from the medical implement through the inlet lumen.

20. The method for supplying fluid through a needleless injection port valve of claim 19, wherein the inlet connector assembly is welded to the valve housing along the sealing seam.

21. The method for supplying fluid through a needleless injection port valve of claim 18, further comprising moving the valve stem from a first position to a second position when the medical implement is inserted through the inlet lumen of the inlet connector assembly.

22. The method for supplying fluid through a needleless injection port valve of claim 21, wherein the valve stem automatically returns to the first position upon removal of the medical implement.

* * * * *